United States Patent [19]
Takahashi et al.

[11] Patent Number: 5,536,448
[45] Date of Patent: Jul. 16, 1996

[54] DENDRITE OR ASTEROIDAL TITANIUM DIOXIDE MICRO-PARTICLES

[75] Inventors: Hideo Takahashi; Akihito Sakai; Masakazu Hattori, all of Yokkaichi, Japan

[73] Assignee: Ishihara Sangyo Kaisha, Ltd., Osaka, Japan

[21] Appl. No.: 326,712

[22] Filed: Oct. 20, 1994

[30] Foreign Application Priority Data

Oct. 22, 1993 [JP] Japan ................................ 5-287467
Nov. 10, 1993 [JP] Japan ................................ 5-305837
Dec. 24, 1993 [JP] Japan ................................ 5-347651

[51] Int. Cl.$^6$ ................... C04B 35/462; C04B 35/478; C09C 1/36; H01H 1/08
[52] U.S. Cl. .................. 252/520; 106/438; 106/441; 106/442; 106/437; 428/402; 428/403; 428/404; 501/134; 423/610
[58] Field of Search .................. 252/520; 428/402, 428/403, 404; 502/350, 351, 352; 501/134; 423/610, 611, 612, 613, 614, 615, 616; 106/437, 438, 441, 442

[56] References Cited

U.S. PATENT DOCUMENTS

| | | | |
|---|---|---|---|
| 2,479,637 | 8/1949 | Olson | 423/616 |
| 2,980,510 | 4/1961 | Berry | 423/613 |
| 3,579,310 | 5/1971 | Lewis et al. | 423/610 X |
| 4,373,013 | 2/1983 | Yoshizumi | 252/518 X |
| 4,880,703 | 11/1989 | Sakamoto et al. | 252/518 X |
| 4,927,464 | 5/1990 | Cowie | 106/442 X |
| 5,068,056 | 11/1991 | Robb | 106/442 X |
| 5,100,858 | 3/1992 | Chopin et al. | 502/350 |
| 5,215,580 | 6/1993 | Elfenthal et al. | 106/441 |
| 5,346,870 | 9/1994 | Noguchi et al. | 501/134 X |
| 5,403,513 | 4/1995 | Sato et al. | 106/437 X |

FOREIGN PATENT DOCUMENTS

| | | |
|---|---|---|
| 341703 | 11/1989 | European Pat. Off. . |
| 0444798 | 9/1991 | European Pat. Off. . |
| 2002112 | 10/1969 | France . |
| 59-6235A | 1/1984 | Japan . |

OTHER PUBLICATIONS

*The New Encyclopædia Britannica Micropædia*, 15 ed., 1994, vol. 1, pp. 650–651.
Derwent WPI, Derwent Publications Ltd., London, GB; AN 87-220300 & SU-A-1 275 001 (SADYKOV R M), abstract.

*Primary Examiner*—Douglas J. McGinty
*Attorney, Agent, or Firm*—Cushman Darby & Cushman

[57] ABSTRACT

Dendrite or asteroidal titanium dioxide micro-particles having a length of 0.2 to 0.5 µm, a thickness of 0.05 to 0.1 µm, and a specific surface area of 20 to 130 $m^2$/gram, are produced by treating hydrated titanium oxide particles with an alkali, mixing instantaneously the resulting reaction product with an amount of hydrochloric acid in a ratio of 1 to 4 mols of hydrochloric acid to one mol of the titanium oxide in the reaction product to effect a reaction, then aging under heat at 85° C. or higher, and then drying or, if necessary, firing after the drying, and subsequently may be coated with at least one from oxides and hydrated oxides of elements selected from aluminum, silicon, titanium, zirconium, tin and antimony to improve the dispersibility and resistance to light of the particles, or may be coated with tin oxide containing antimony or indium oxide containing tin to make the particles electroconductive. These titanium dioxide micro-particles are useful for use in electroconductive paints, electroconductive resin compositions, paints and electroconductive paints for magnetic recording media, sunscreen cosmetics, UV screening paints and UV shielding plastic compositions and the like.

9 Claims, 2 Drawing Sheets

5,536,448

DENDRITE OR ASTEROIDAL TITANIUM DIOXIDE MICRO-PARTICLES

BACKGROUND OF THE INVENTION

1. Field of the Invention

The present invention relates to dendrite or asteroidal titanium dioxide micro-particles, a process for producing the same, electroconductive dendrite or asteroidal titanium dioxide micro-particles comprising said titanium dioxide micro-particles as substrate which have been subjected to an electroconductivity imparting treatment, and a process for producing the same. The titanium dioxide micro-particles according to the present invention are useful for sunscreen preparations or cosmetics, UV screening paints, UV screening or shielding materials in plastics, electroconductivity imparting or antistatic materials to be used in plastics, paints, rubbers and fibers, as well as electroconductivity imparting agents or substrates to be used in supports for recording materials such as electrophotographic copying paper and electrostatographic recording paper.

2. Description of the Related Art

Fine titanium dioxide particles having a primary particle size of 0.1 μm or less are transparent because they transmit rays of visible light when incorporated in resin films or shapes, and on the other hand capable of shielding ultraviolet radiation to protect materials which may be discolored or degenerated with ultraviolet radiation. Thus they have different properties from those of pigment titanium dioxide having a primary particle size of about 0.15 to 0.5 μm so that they have been utilized in sunscreen preparations, UV screening paints, and UV screening or shielding materials for plastics.

With respect to the transparency and UV shielding property of the aforementioned titanium dioxide micro-particles, the former property increases inversely proportional to the particle size, while the latter varies with the particle size with reaching a maximum in a specific range of the particle size and then decreasing as the particle size increases over the specific range. That is, the UV shielding property is reduced at particle sizes either smaller or larger than the specific range. Therefore, development of titanium dioxide micro-particles having simultaneously satisfactory transparency and UV shielding property has been desired.

The aforementioned titanium oxide micro-particles having a average primary particle size of about 0.05 to 0.1 μm have been produced by, for example, a process comprising firing hydrated titanium dioxides produced by hydrolyzing a solution of titanyl sulfate or titanium tetrachloride, or a titania sol obtained by thermally treating the hydrated titanium dioxides in the presence of hydrochloric acid after treated with a caustic alkali. However, sintering of particles are highly apt to occur in the course of the firing process, so that it is difficult to achieve substantial dispersion of the primary particles in various media for numerous applications resulting in unsatisfactory UV shielding effect which is vigorously desired to be improved.

Titanium oxide compounds which have been proposed as electroconductivity imparting materials include (1) spherical electroconductive titanium oxide particles which substrates are spherical titanium oxide particles or fine spherical titanium oxide particles, (2) electroconductive materials comprising primarily fibrous potassium titanate, and (3) acicular electroconductive titanium oxide particles based on high quality acicular titanium oxide particles having a length of 1 to 10 μm.

Generally speaking, electrical conductivity-impartig materials of an acicular form (including fibrous form), as compared with spherical form, and furthermore the materials which are lower in their powder resistivity, namely, higher in electrical conductivity, can give resin articles and rubber articles of the desired conductivity even with the addition thereof in a small amount to the article. The spherical electroconductive titanium oxide particles referred to in the above item (1) are generally required to be incorporated in a considerably large amount into media such as resins and rubbers to impart desired electroconductivities to the media due to spherical particles, though their powder bodies have a very excellent electroconductivity, for example, a resistivity of 1 to 10 Ω cm. For this reason, the use of spherical titanium oxide particles produces problems of reducing the strength of the products such as electroconductive resins and rubbers and of being uneconomical. The electroconductive materials referred to in the above item (2) have no problem in configuration, but disadvantages that the powder body of the materials has a high resistivity and the fibrous materials are liable to break during dispersing. Acicular electroconductive titanium oxide particles referred to in the above item (3) overcome the problems described above with respect to (1) and (2) in that only a small amount of the acicular particles is required to be added to achieve a very excellent electroconductivity, but they cause problems of flatness of the surfaces of coatings obtained by spreading a paint composition containing the acicular particles and a medium on a substrate, because they are too long in addition to being acicular. There is a need for titanium oxide particles which are useful for an antistatic agent for magnetic recording media, more excellent in transparency and surface flatness of magnetic layers as well as in electroconductivity imparting effect according to a demand for increasing recording density.

SUMMARY OF THE INVENTION

An object of the present invention is to provide titanium dioxide micro-particles having a specific length, a specific thickness, a specific surface area and a specific configuration and a process for producing the same.

Another object of the present invention is to provide a process for producing dendrite or asteroidal titanium dioxide micro-particles having a length of 0.2 to 0.5 μm, a thickness of 0.05 to 0.1 μm, and a specific surface area of 20 to 130 m$^2$/gram comprising treating hydrated titanium oxide particles with alkali, mixing instantaneously the resulting reaction product with an amount of hydrochloric acid in a ratio of 1 to 4 mols of hydrochloric acid to one mol of the titanium oxide in said reaction product to effect a reaction, then aging under heat at 85° C. or higher, and then drying or, if necessary, firing after the drying.

Still another object of the present invention is to provide dendrite or asteroidal titanium dioxide micro-particles, which are further improved in dispersibility in media as well as in resistance to light, having a layer of at least one selected from oxides and hydrated oxides of elements selected from the group consisting of aluminum, silicon, titanium, zirconium, tin and antimony coated on the surfaces of the particles.

Still another object of the present invention is to provide a process for producing dendrite or asteroidal titanium dioxide micro-particles, which are further improved in dispersibility in media as well as in resistance to light, comprising forming a slurry of the dendrite or asteroidal titanium dioxide micro-particles, adding to the slurry at least one selected from the group consisting water soluble salts of each element selected from aluminum, silicon, titanium, zirconium, tin and antimony, neutralizing the resultant slurry to coat the surfaces of said titanium dioxide micro-particles with at least one selected from oxides and hydrated oxides of said elements.

Still another object of the present invention is to provide electroconductive dendrite or asteroidal titanium dioxide micro-particles comprising the dendrite or asteroidal titanium dioxide micro-particles having an electroconductive layer of tin oxide containing antimony or indium oxide containing tin coated on the surfaces of the particles.

Still another object of the present invention is to provide an electroconductive paint, electroconductive resin composition, paint for magnetic recording media, electroconductive paint for magnetic recording media, sunscreen cosmetic, UV screening paint, UV shielding plastic composition, and the like which comprise the dendrite or asteroidal titanium dioxide micro-particles

DETAILED DESCRIPTION OF THE INVENTION

Figure 1:
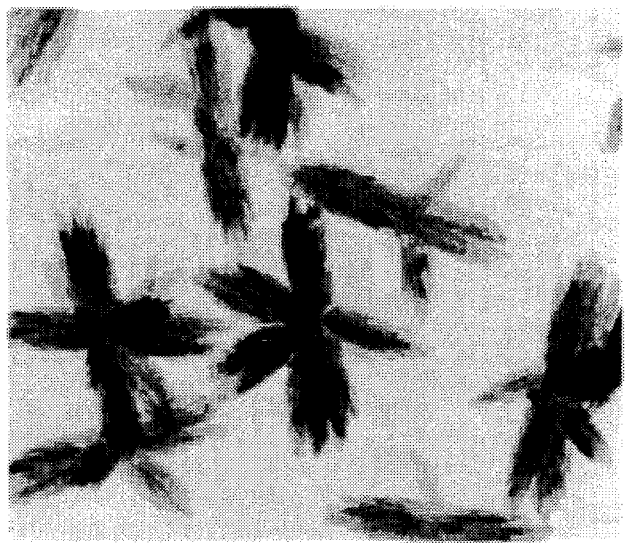
FIG. 1 is an electron microphotograph (a magnification of 100,000) showing the grain structure of the dendrite or asteroidal titanium dioxide micro-particles (Sample A) of the present invention produced in the step (2) of Example 1.
Figure 2:
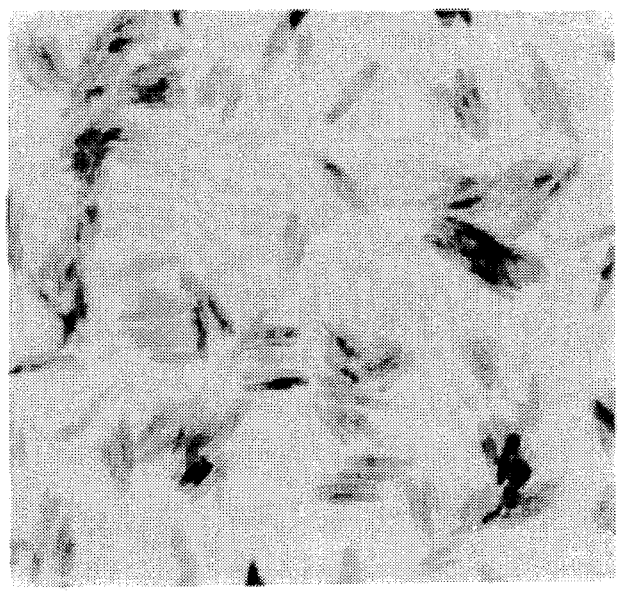
FIG. 2 is an electron microphotograph (a magnification of 100,000) showing the grain structure of the dendrite or asteroidal titanium dioxide micro-particles (Sample B) of the present invention produced in the step (3) of Example 1.
Figure 3:
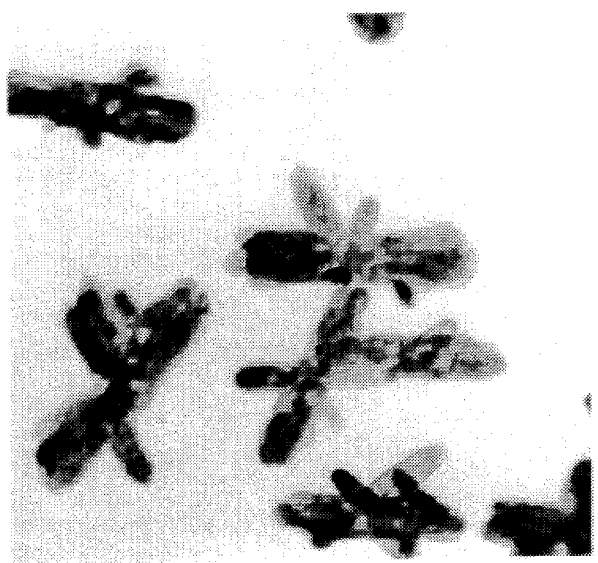
FIG. 3 is an electron microphotograph (a magnification of 100,000) showing the grain structure of the rod type titanium dioxide micro-particles (Sample C) produced in the step (2) of Comparative Example 1.
Figure 4:
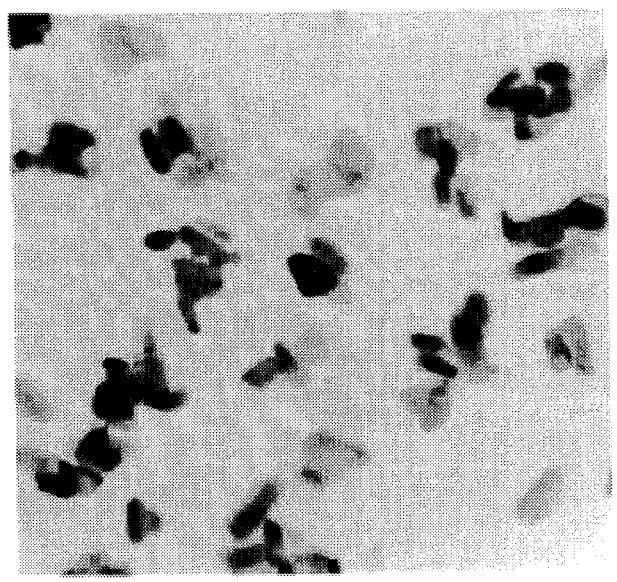
FIG. 4 is an electron microphotograph (a magnification of 100,000) showing the grain structure of the rod type titanium dioxide micro-particles (Sample D) produced in the step (3) of Comparative Example 1.

The present inventors have made an intensive research to overcome the aforementioned difficulties, and as a result, it has been found that titanium dioxide micro-particles having a specific length, a specific thickness, a specific surface area and a specific configuration, which can be produced under specific conditions, have an excellent UV shielding property and are good in transparency and surface flatness in application systems, and that none of sintering and great deformation of particles are caused by firing to allow the particles to possess good UV shielding property, excellent resistance to light, superior transparency and surface flatness in application systems, and that the titanium dioxide micro-particle substrate may be subjected to an electroconductivity imparting treatment to produce an electroconductivity imparting agent having an extremely excellent performance which can find a great many potential applications. The present invention is accomplished based on the above findings.

That is, the present invention relates to (1) a process for producing dendrite or asteroidal titanium dioxide micro-particles comprising treating hydrated titanium oxide particles with an alkali, mixing instantaneously the resulting reaction product with an amount of hydrochloric acid in a ratio of 1 to 4 mols of hydrochloric acid to one mol of the titanium oxide in the reaction product to effect a reaction, then aging under heat at 85° C. or higher, and then drying or, if necessary, firing after drying, (2) a process for producing dendrite or asteroidal titanium dioxide micro-particles comprising forming a slurry of the dendrite or asteroidal titanium dioxide micro-particles obtained by the above process (1), adding to the slurry at least one selected from the group consisting water soluble salts of each element selected from aluminum, silicon, titanium, zirconium, tin and antimony, neutralizing the resultant slurry to coat the surfaces of said titanium dioxide micro-particles with at least one selected from oxides and hydrated oxides of said elements, (3) dendrite or asteroidal titanium dioxide micro-particles having a length of 0.2 to 0.5 μm, a thickness of 0.05 to 0.1 μm, and a specific surface area of 20 to 130 $m^2$/gram, which are produced by the above process (1), (4) products obtained by the above process (2), and (5) electroconductive paints, electroconductive resin composition, magnetic recording medium paints, electroconductive paints for magnetic recording medium, sunscreen cosmetics, UV screening paints and UV shielding plastic compositions, which are prepared using the aforementioned products.

The dendrite or asteroidal titanium dioxide micro-particles according to the present invention have a dendrite or asteroidal configuration, where acicular and/or rod type particles assemble or combine to form a bundle shape and then a plurality of bundle shapes combine radially to form a single composite particle, which is completely different from conventional acicular, rod-like or spherical as is apparent from Figures (electron microphotographs). As used here in connection with such configuration, the term "length" of the dendrite or asteroidal titanium dioxide micro-particles according to the present invention means the longest dimension of each single composite particle, and the term "thickness" means the largest diameter in the direction of a short axis of the bundle shape composing the longest part. The dendrite or asteroidal titanium oxide particles of the present invention have a length of 0.2 to 0.5 μm, a thickness of 0.05 to 0.1 μm and a specific surface area of 20 to 130 $m^2$/gram. As described later, when the titanium dioxide micro-particles are employed as substrate particles, subjected to an electroconductive coating treatment and then fired, the specific surface area of the particulate titanium oxide substrate should be in the range of 70 $m^2$/gram to 130 $m^2$/gram, preferably in the range of 70 $m^2$/gram to 100 $m^2$/gram, while when the fired titanium dioxide micro-particles are employed as substrate particles, subjected to the electroconductive coating treatment, and further fired, the specific surface area of the particulate titanium oxide substrate should be in the range of 20 $m^2$/gram to less than 70 $m^2$/gram, preferably 20 $m^2$/gram to 50 $m^2$/gram.

The dendrite or asteroidal titanium dioxide micro-particles of the present invention are useful for various sunscreen preparations, UV screening paints, and UV shielding plastic compositions, and may be further improved in dispersibility and resistance to light of the titanium oxide particles in the dispersion thereof in medium by depositing at least one from hydrated oxides of metals such as aluminum, silicon, titanium, zirconium, tin and antimony onto the surfaces of the micro-particles. The amount of the oxides or hydrated oxides of metals to be deposited should be in the range from 1 to 100% by weight expressed as a total of metal oxides based on the titanium dioxide.

The dendrite or asteroidal titanium dioxide micro-particles of the present invention which have been subjected to the electroconductive coating treatment may be incorporated as electroconductivity imparting agent or substrates into plastics, rubbers, fibers and the like, to produce usable electroconductive compositions such as electroconductive plastics, electroconductive paints, magnetic paints, electroconductive rubbers, electroconductive fibers and the like. The electroconductive coating treatment may be accomplished by forming an electroconductive layer comprising tin oxide doped with antimony or indium oxide doped with tin on the surfaces of the dendrite or asteroidal titanium dioxide micro-particles. The formation of the electroconductive layer may be performed by, for example, adding a water soluble tin compound and a water soluble antimony compound to the titanium dioxide micro-particles to deposit hydrated tin oxide and hydrated antimony oxide onto the surfaces of the titanium dioxide micro-particles, and then firing to form the electroconductive layer comprising tin oxide doped with antimony. In this case, the amount of tin oxide should be in the range from 10 to 150% by weight, preferably 30 to 100% by weight as $SnO_2$. An amount of tin oxide lower than the indicated range may make it difficult to form continuous electroconductive layer with no desired electroconductivity being achieved. Addition of too much tin oxide is uneconomical because further improvement in electroconductivity corresponding to an increase in the amount over the indicated range can not be expected. The amount of the aforementioned antimony oxide in the electroconductive layer should be in the range from 5 to 40% by weight, preferably 10 to 30% by weight as $Sb_2O_3$ based on tin oxide ($SnO_2$). An amount of antimony oxide lower than the stated range may result in impossibility of attaining desired electroconductivity. Too high an amount of antimony oxide is undesirable because it may cause reduced electroconductivity and intensive coloration with antimony oxide.

A process for producing the dendrite or asteroidal titanium dioxide micro-particles according to the present invention is described under.

First, an alkali is added to an aqueous dispersion of hydrated titanium oxide and then heated at a temperature of 90° to 100° C. to produce a reaction product, the pH of which is adjusted to neutral to separate solid from liquid, and then the solid is washed with water. The alkalis to be used in the treatment with alkali include sodium hydroxide and sodium carbonate, and the use of an aqueous solution of sodium hydroxide is preferred. The aforementioned washed reaction product is dispersed in water to produce a dispersion. The dispersion and hydrochloric acid are instantaneously mixed in a ratio of hydrochloric acid of 1 to 4 mols relative to one mol of the titanium oxide in the dispersion to effect a reaction. More practically speaking, for example, the hydrochloric acid is added to the dispersion at a speed of at least 2 mols/second with stirring in a ratio of hydrochloric acid of 1 to 4 mols to one mol of the titanium oxide of the reaction product in the dispersion. Alternatively, the dispersion and hydrochloric acid are placed at a time in a vessel in the ratio as described above and mixed with stirring. If desired, the dispersion may be incorporated into the hydrochloric acid. Then the resulting dispersion is aged at a temperature of 85° to 100° C., preferably 90° to 100° C. for one hour or more to produce an aqueous dispersion of dendrite or asteroidal titanium dioxide micro-particles which is filtrated, washed and dried to produce powdery dendrite or asteroidal titanium dioxide micro-particles, and if necessary, the powder may be fired at a temperature of 400° to 700° C. to produce a powder of dendrite or asteroidal titanium dioxide micro-particles.

The hydrated titanium oxides, a titanium source of the dendrite or asteroidal titanium dioxide micro-particles include those obtained from the hydrolysis or the hydrolysis under neutralization of a solution of titanyl sulfate or a solution of titanium tetrachloride. More practically, for example, an aqueous solution of titanium tetrachloride is neutralized with an aqueous solution of sodium hydroxide while maintaining at room temperature to precipitate colloidal amorphous titanium hydroxide which is aged under heat to produce a fine rutile titania sol for practical use.

Onto the surfaces of the dendrite or asteroidal titanium dioxide micro-particles obtained as described above, there may be deposited or coated at least one of oxides and hydrated oxides of metals such as aluminum, silicon, titanium, zirconium, tin and antimony. This coating treatment may be accomplished by, for example, dispersing the dendrite or asteroidal titanium dioxide micro-particles into water to produce a slurry, and if necessary, wet ground and classified, and thereafter at least one selected from the group consisting of water soluble salts of aluminum, silicon, titanium, zirconium, tin and antimony is added to the slurry in an amount of 1 to 100 expressed as a total amount of oxides based on the titanium dioxide, and then the slurry is neutralized with an acidic solution such as sulfuric acid, hydrochloric acid and the like when the addition of the water soluble salts renders the dispersion alkaline, or with a basic solution such as an aqueous alkaline solution of sodium hydroxide, ammonia water and the like when the addition of the water soluble salts renders the dispersion acidic, to effect the coating deposition onto the surfaces of the titanium dioxide micro-particles which then are separated, dried and ground. This coating treatment allows improvement in dispersibility and durability of the dendrite or asteroidal titanium dioxide micro-particles in dispersion media.

As described above, the dendrite or asteroidal titanium dioxide micro-particles of the present invention are useful for various sunscreen cosmetics, UV screening paints, and UV shielding plastic compositions, and the electroconductive dendrite or asteroidal titanium dioxide micro-particles which have been subjected to the electroconductive imparting treatment may be incorporated as electroconductivity imparting agent or substrates into plastics, rubbers, fibers and the like, to produce usable electroconductive compositions such as electroconductive plastics, electroconductive paints, magnetic paints, electroconductive rubbers, electroconductive fibers and the like.

The dendrite or asteroidal titanium dioxide micro-particles of the present invention can be used in sunscreen cosmetics in any one of various forms such as lotion, cream, paste, stick and emulsion, into which additives such as oily components, moisturizing agents, surfactants, flavors, preservatives, water, alcohols and thickners may be incorporated.

The dendrite or asteroidal titanium dioxide micro-particles can be used in production of UV screening plastics or electroconductive plastics by incorporating into synthetic resins such as vinyl chloride resins, ABS resins, polyethylenes, polypropylenes, vinylidene chloride, polystyrenes, polycarbonates, nylon, EVA resins, polyacetal resins, polyamide resins, phenolic resins, melamine resins, acrylic resins, polyester resins, urea resins, silicone resins and fluorinated resins.

When the dendrite or asteroidal titanium dioxide micro-particles can be used in UV screening paints, electroconductive paints or magnetic paints, they are incorporated into, for example, polyvinyl alcohol resins, vinyl chloride-vinyl acetate resins, acrylic resins, epoxide resins, urethane resins, alkyd resins, polyester resins, ethylene vinyl acetate copolymers, acrylic styrene copolymers, cellulose resins, phenolic resins and amino resins, by dispersing in water or solvents, With electroconductive paints, they may be coated on an insulating substrate such as a sheet of paper and polymer films to form a light electroconductive coating having an excellent adherence on the surfaces thereof which can be used as electrostatic recording paper, electrophotographic copying paper and antistatic films.

The paints to be used in production of magnetic recording media are useful for improving adhesion strength between a non-magnetic support and a magnetic layer, antistatic property of magnetic recording media, film strength, thinner magnetic layer, dispersibility of non-magnetic underlayer accompanied with surface flattening, and surface flatness. Among others, a recent tendency of increasing the recording density in magnetic recording requires remarkably shorter and shorter wavelengths for recording, which is accompanied with the requirement of making the magnetic layer of magnetic recording media thinner. However, the reducing of the thickness of the magnetic layer tends to cause manifestation of influence of the support onto the surfaces of the magnetic layer resulting inevitably in deterioration in electromagnetic properties. For this reason, for example, an attempt has been made to avoid the influence of the surface roughness of the support by providing a non-magnetic undercoat layer on the surface of the non-magnetic support and then a magnetic overcoat layer on the undercoat layer, simultaneously making the magnetic layer thinner to increase the output. In this connection, the dendrite or asteroidal titanium dioxide micro-particles of the present invention may be filled in the non-magnetic undercoat layer to render the surface flatness of the magnetic overcoat layer more preferable. The proportion of the titanium dioxide micro-particles to be filled in the non-magnetic undercoat layer should be on the order of 20 to 80% by volume.

The dendrite or asteroidal titanium dioxide micro-particles of the present invention can be used in production of electroconductive rubbers, for example, by incorporating into known conventional elastomers such as silicone rubbers, isoprene rubbers, styrene-butadiene rubbers, butadiene rubbers, butyl rubbers, butadiene-acrylonitrile rubbers, ethylene-propylene-diene polymers, ethylene-propylene rubbers, fluorinated rubbers, ethylene-vinyl acetate copolymers, chlorinated polyethylenes, acrylic rubbers, chloroprene rubbers, urethane rubbers, polysulfide rubbers, chlorosulfonated polyethylene rubbers, and epichlorohydrin rubbers.

The dendrite or asteroidal titanium dioxide micro-particles of the present invention can be used in production of electroconductive fibers, for example, by incorporating into spinnable resins such as polyamide resins, polyester resins, polyolefin resins, polyvinyl resins and polyether resins.

The thus obtained electroconductive compositions are advantageous in cost because less amount thereof to be incorporated into resin binders is required to achieve a high electroconductivity than the conventional electroconductive compositions formulated with spherical electroconductive particles. Since such a small amount of the compositions to be incorporated is required, they can be utilized without causing any reduction in strength of the binders. Electroconductive paints having a high concentration of the compositions enable attainment of desired electroconductivity with a thinner coating film.

The dendrite or asteroidal titanium dioxide micro-particles of the present invention can be used in various cosmetics and paints where they may be coated with at least one of organic agents for treatments to be used in the fields of preparations and paints such as carboxylic acids, polyhydrics, amines, siloxanes and silane coupling agents, whereby they may be improved in the dispersibility into cosmetics and paints as well as the durability of coating films.

EXAMPLE 1

(1) Hydrated titanium oxide particles obtained by hydrolysis of an aqueous solution of titanium tetrachloride were dispersed in a concentration of 100 grams/liter expressed as $TiO_2$ to produce an aqueous dispersion. To 2 liters of this dispersion there were added 1400 grams of an aqueous 48% sodium hydroxide solution with stirring, the mixture was heated at 95° C. for 120 minutes, filtered and sufficiently washed. The washed cake was repulped in water to produce an aqueous dispersion having a concentration of 100 grams/liter expressed as $TiO_2$. 1.5 liters of this aqueous dispersion were placed in a flask equipped with a reflux condenser and 570 grams of a 35% hydrochloric acid were instantaneously added with stirring at a speed of 4 mols/second, and thereafter the mixture was aged under heat at 95° C. for 120 minutes to produce an aqueous dispersion containing dendrite or asteroidal titanium dioxide micro-particles.

(2) The aqueous dispersion obtaind in the above step (1) was filtered, washed, and the resultant washed cake was dried at 120° C. for one whole day and night to produce dendrite or asteroidal titanium dioxide micro-particles having a rutile crystal length of 0.30 μm, a thickness of 0.055 μm, a specific surface area of 79 $m^2$/gram (Sample A).

(3) The aqueous dispersion containing dendrite or asteroidal titanium dioxide micro-particles obtaind in the above step (1) was filtered, washed, and the resultant washed cake was dried at 120° C. for one whole day and night, followed by firing in an electric furnace at 500° C. for one hour to produce dendrite or asteroidal titanium dioxide micro-particles having a length of 0.27 μm, a thickness of 0.05 μm, a specific surface area of 28 $m^2$/gram (Sample B).

COMPARATIVE EXAMPLE 1

(1) Hydrated titanium oxide particles obtained by hydrolysis of an aqueous solution of titanium tetrachloride were dispersed in a concentration of 100 grams/liter expressed as $TiO_2$ to produce an aqueous dispersion. To 2 liters of this dispersion there were added 1400 grams of an aqueous 48% sodium hydroxide solution with stirring, the mixture was heated at 95° C. for 120 minutes, then filtered and sufficiently washed. The washed cake was repulped in water to produce an aqueous dispersion having a concentration of 100 grams/liter expressed as $TiO_2$. 1.5 liters of this aqueous dispersion were placed in a flask equipped with a reflux condenser and 570 grams of a 35% hydrochloric acid were added over 30 minutes with stirring, and thereafter the mixture was heated to 95° C. and aged for 90 minutes to produce an aqueous dispersion containing rod type titanium dioxide micro-particles.

(2) The aqueous dispersion obtained in the above step (1) was filtered, washed, and the resultant washed cake was dried at 120° C. for one whole day and night to produce rod type titanium dioxide micro-particles having a rutile crystal length of 0.07 μm, an aspect ratio of 7, a specific surface area of 99 $m^2$/gram (Sample C).

(3) The aqueous dispersion containing rod type titanium dioxide micro-particles obtained in the above step (1) was filtered, washed, and the resultant washed cake was dried at 120° C. for one whole day and night, followed by firing in an electric furnace at 500° C. for one hour to produce rod type titanium dioxide micro-particles having a length of 0.07 μm, a thickness of 0.035 μm, a specific surface area of 39 m$^2$/gram (Sample D).

EXAMPLE 2

The aqueous dispersion containing dendrite or asteroidal titanium dioxide micro-particles obtained in the above step (1) of Example 1 was heated to 90° C., and a solution of 150 grams of tin chloride (SnCl$_4$.5H$_2$O) and 25 grams of antimony chloride (SbCl$_3$) dissolved in 200 milliliters of an aqueous 6N hydrochloric acid solution was added to the heated dispersion together with an aqueous 10% sodium hydroxide solution over 60 minutes so as to keep the pH of the dispersion at 2 to 3, thereby depositing hydrates of tin oxide and antimony oxide onto the surfaces of the dendrite or asteroidal titanium dioxide micro-particles. In this case, the final pH of the dispersion was 3. Then the aqueous dispersion of the coated dendrite or asteroidal titanium dioxide micro-particles was filtered, washed until the conductivity of the filtrate reached less than 50 μS, the cake of the coated dendrite or asteroidal titanium dioxide micro-particles was dried at 120° C. for a whole day and night and then fired in an electric furnace at 500° C. for one hour to produce electroconductive dendrite or asteroidal titanium dioxide micro-particles having an electroconductive layer of tin oxide doped with antimony, which comprised by weight 51.6% SnO$_2$ and 13.3% Sb$_2$O$_3$ based on the weight of TiO$_2$, coated on the surfaces and having a length of 0.36 μm, a thickness of 0.065 μm and a specific surface area of 33 m$^2$/gram (Sample E). Its powder resistance was determined to be 13 Ω cm.

The dendrite or asteroidal titanium dioxide micro-particles obtained in the above step (3) of Example 1 were dispersed in water to produce an aqueous dispersion having a concentration of 100 grams/liter expressed as TiO$_2$, and one liter of the dispersion was wet ground, heated to 90° C., and a solution of 100 grams of tin chloride (SnCl$_4$.5H$_2$O) and 17 grams of antimony chloride (SbCl$_3$) dissolved in 200 milliliters of an aqueous 6N hydrochloric acid solution was added to the heated dispersion together with an aqueous 10% sodium hydroxide solution over 60 minutes so as to keep the pH of the dispersion at 2 to 3, thereby depositing hydrates of tin oxide and antimony oxide onto the surfaces of the dendrite or asteroidal titanium dioxide micro-particles. In this case, the final pH of the dispersion was 3. Then the aqueous dispersion of the coated dendrite or asteroidal titanium dioxide micro-particles was filtered, washed until the conductivity of the filtrate reached less than 50 μS, the cake of the coated dendrite or asteroidal titanium dioxide micro-particles was dried at 120° C. for a whole day and night and then fired in an electric furnace at 500° C. for one hour to produce electroconductive dendrite or asteroidal titanium dioxide micro-particles having an electroconductive layer of tin oxide containing antimony, which comprised by weight 51.7% SnO$_2$ and 13.4% Sb$_2$O$_3$ based on the weight of TiO$_2$, coated on the surfaces and having a length of 0.29 μm, a thickness of 0.05 μm and a specific surface area of 33 m$^2$/gram (Sample F). Its powder resistance was determined to be 8.0 Ω cm.

Its powder resistance was determined by first forming a powdery sample under a pressure of 100 Kg/cm$^2$ to a cylindrical pressed body of dimensions of 18 mm in diameter×3 mm in thickness, and then measuring the DC resistivity of the body according to the following formula:

$$\text{Its powder resistance } [\Omega \cdot \text{cm}] = \text{Measurement } [\Omega] \times \frac{2.54 \, [\text{cm}^2]}{0.3 \, [\text{cm}]}$$

COMPARATIVE EXAMPLE 2

The aqueous dispersion containing rod type titanium dioxide micro-particles obtained in the above step (1) of Comparative Example 1 was heated to 90° C., and a solution of 150 grams of tin chloride (SnCl$_4$.5H$_2$O) and 25 grams of antimony chloride (SbCl$_3$) dissolved in 200 milliliters of an aqueous 6N hydrochloric acid solution was added to the heated dispersion together with an aqueous 10% sodium hydroxide solution over 60 minutes so as to keep the pH of the dispersion at 2 to 3, thereby depositing hydrates of tin oxide and antimony oxide onto the surfaces of the rod type titanium dioxide micro-particles. In this case, the final pH of the dispersion was 3. Then the aqueous dispersion of the coated rod type titanium dioxide micro-particles was filtered, washed until the conductivity of the filtrate reached less than 50 μS, the cake of the coated rod type titanium dioxide micro-particles was dried at 120° C. for a whole day and night and then fired in an electric furnace at 500° C. for one hour to produce electroconductive rod type titanium dioxide micro-particles having an electroconductive layer of tin oxide containing antimony, which comprised by weight 47.2% SnO$_2$ and 11.6% Sb$_2$O$_3$ based on the weight of TiO$_2$, coated on the surfaces and having a length of 0.1 μm, a thickness of 0.015 μm and a specific surface area of 41 m$^2$/gram (Sample G). Its powder resistance was determined to be 15 Ω cm.

The rod type titanium dioxide micro-particles obtained in the above step (3) of Comparative Example 1 were dispersed in water to produce an aqueous dispersion having a concentration of 100 grams/liter expressed as TiO$_2$, and one liter of the dispersion was wet ground, heated to 90° C., and a solution of 100 grams of tin chloride (SnCl$_4$.5H$_2$O) and 17 grams of antimony chloride (SbCl$_3$) dissolved in 200 milliliters of an aqueous 6N hydrochloric acid solution was added to the heated dispersion together with an aqueous 10% sodium hydroxide solution over 60 minutes so as to keep the pH of the dispersion at 2 to 3, thereby depositing hydrates of tin oxide and antimony oxide onto the surfaces of the rod type titanium dioxide micro-particles. In this case, the final pH of the dispersion was 3. Then the aqueous dispersion of the coated rod type titanium dioxide micro-particles was filtered, washed until the conductivity of the filtrate reached less than 50 μS, the cake of the coated rod type titanium dioxide micro-particles was dried at 120° C. for a whole day and night and then fired in an electric furnace at 500° C. for one hour to produce electroconductive rod type titanium dioxide micro-particles having an electroconductive layer of tin oxide containing antimony, which comprised by weight 51.0% SnO$_2$ and 13.1% Sb$_2$O$_3$ based on the weight of TiO$_2$, coated on the surfaces and having a length of 0.07 μm, a thickness of 0.04 μm and a specific surface area of 29 m$^2$/gram (Sample H). Its powder resistance was determined to be 12 Ω cm.

EXEMPLARY TEST 1

The titanium dioxide micro-particles of Samples A and C obtained in Example 1 and Comparative Example 1 were each incorporated in the following formulation to produce a sunscreen cream:

|     |                              | parts by weight |
| --- | ---------------------------- | --------------- |
| (1) | Stearic acid                 | 2.5             |
| (2) | Bleached bees wax            | 3.5             |
| (3) | Cetanol                      | 3.5             |
| (4) | Squalene                     | 17.0            |
| (5) | Glycerin monostearate        | 3.0             |
| (6) | Titanium dioxide micro-particles | 3.0         |
| (7) | Methylparaben                | 0.1             |
| (8) | Glycerin                     | 12.0            |
| (9) | Triethanolamine              | 1.0             |
| (10)| Distilled water              | 54.1            |
| (11)| Flavor                       | 0.3             |

The components (1) to (6) were mixed under heat at 80° C. and added to a mixture of components (7) to (10) mixed under heat at 80° C., and the whole was intimately mixed by a homogenizing mixer and vigorously stirred. The flavor (11) was added at around 45° C. to prepare a sunscreen cream.

EVALUATION

Each of the creams was coated on a quartz glass sheet to a film thickness of 25 μm and evaluated for transmittance with a spectrophtometer at a wave length of 750 to 300 nm. The results of the evaluation are shown in Table 1.

TABLE 1

|            |        | Transmittance (%)              |                      |                      |
| ---------- | ------ | ------------------------------ | -------------------- | -------------------- |
|            | Sample | Visible light range (550 nm)   | UV A range (375 nm)  | UV B range (300 nm)  |
| Example 1  | A      | 61.6                           | 16.7                 | 7.8                  |
| Comp. Ex. 1| C      | 85.9                           | 56.7                 | 41.5                 |

EXEMPLARY TEST 2

(1) 20 grams of each of the Samples E, F, G and H obtained in Example 2 and Comparative Example 2 were added to a glass bottle containing 30.6 grams of acrylic resin (Acrydic A-165-45; 45% by weight solids, available from Dainihon Ink Chemical Industry Co.), 16.4 grams of a liquid mixture of toluene/butanol (1/1) and 50 grams of glass beads and the whole was shaken for 30 minutes with a paint shaker to produce a dispersion to be used as a mill base.

(2) To each mill base was added the acrylic resin and the liquid mixture of toluene/butanol identical to those described above to attain a concentration of each pigment of 20%, 30%, and 40%, to prepare a paint. The paint was applied on a sheet of art paper to a film thickness of 37 μm on dryness and dried for 40 hours to produce a specimen. The art paper specimens were evaluated for electric resistance by a digital ohm meter (Model R-506 available from Kawaguchi Electric Manufacturing) and the surface resistivity was calculated according to the following formula:

Surface resistivity $[\Omega/\square]$ = Measurement × 50 (Electrode constant)

TABLE 2

| Surface resistivity of the film applied on the art specimen $[\Omega/\square]$ | | | |
| --- | --- | --- | --- |
| | Concentration of pigment in the film [% by weight] | | |
| Sample | 20 | 30 | 40 |
| Example 2   E | $2.3 \times 10^7$ | $4.6 \times 10^6$ | $1.0 \times 10^6$ |
|             F | $1.0 \times 10^7$ | $1.3 \times 10^6$ | $3.2 \times 10^5$ |
| Comp. Ex. 2 G | $5.2 \times 10^7$ | $8.0 \times 10^6$ | $2.3 \times 10^6$ |
|             H | $3.6 \times 10^7$ | $3.2 \times 10^6$ | $7.0 \times 10^5$ |

EXEMPLARY TEST 3

The titanium dioxide micro-particles of Samples B and D obtained in Example 1 and Comparative Example 1 were evaluated for photocatalytic activity according to the following procedure:

0.2 gram of a sample and 10 cm³ of tetralin were placed in a flat bottom pan type reaction vessel (50 cm³) which then was disposed on a tetralin test apparatus equipped with a water bath, magnetic stirrer, mercury manometer and mercury lamp. The temperature of the water in the bath was kept at 40° C. while stirring with the magnetic stirrer, the valve of the mercury manometer was closed, and the reaction vessel was exposed to the light rays from a 75 W mercury lamp at an illuminance of 2500 lux from above the vessel. During the irradiation, the difference in pressure in the mercury manometer was read every 5 minutes. The results of the evaluation are shown in Table 3.

TABLE 3

|              |        | Irradiation time (min.) | | | | | | | |
| ------------ | ------ | --- | --- | --- | --- | --- | --- | --- | --- |
|              | Sample | 5   | 10  | 15  | 20  | 25  | 30  | 35  | 40  |
| Example 1    | B      | 5   | 10  | 15  | 19  | 25  | 29  | 34  | 39  |
| Comp. Ex. 1  | D      | 6   | 13  | 20  | 25  | 32  | 39  | 46  | 52  |
| Control      | —      | 2   | 5   | 8   | 10  | 12  | 15  | 17  | 20  |

Note: A larger numeral means a higher photocatalytic activity.

The present invention lies in dendrite or asteroidal titanium dioxide micro-particles which can be produced by a simple process comprising treating an aqueous dispersion of hydrated titanium oxide with alkali, then adding rapidly hydrochloric acid to the dispersion which is aged under heat with or without further firing after the aging. On the surfaces of the titanium dioxide micro-particles, various metal compounds may be coated or deposited, whereby the titanium dioxide micro-particles can be rendered useful in UV screening or shielding preparations or paints or as substrate materials capable of imparting electroconductivity. Thus the present invention has a great effect in industry.

What is claimed is:

1. Dendritic or asteroidal titanium dioxide micro-particles having a length of 0.2 to 0.5 μm along a longest dimension of each micro-particle, a thickness of 0.05 to 0.1 μm as the largest diameter in the direction of a short axis of the micro-particle, and a specific surface area of 20 m²/gram to 130 m²/gram.

2. Dendrite or asteroidal titanium dioxide micro-particles according to claim 1, wherein said particles have a specific surface area of 70 m²/gram to 130 m²/gram.

3. Dendrite or asteroidal titanium dioxide micro-particles according to claim 1, wherein said particles have a specific surface area of 20 m²/gram to less than 70 m²/gram.

4. Dendrite or asteroidal titanium dioxide micro-particles comprising the dendrite or asteroidal titanium dioxide micro-particles according to claim 1 having a layer of at least one selected from oxides and hydrated oxides of elements selected from the group consisting of aluminum, silicon, titanium, zirconium, tin and antimony coated on the surfaces of the particles.

5. Dendrite or asteroidal titanium dioxide micro-particles comprising the dendrite or asteroidal titanium dioxide micro-particles according to claim 2 having a layer of at least one selected from oxides and hydrated oxides of elements selected from the group consisting of aluminum, silicon, titanium, zirconium, tin and antimony coated on the surfaces of the particles.

6. Dendrite or asteroidal titanium dioxide micro-particles comprising the dendrite or asteroidal titanium dioxide micro-particles according to claim 3 having a layer of at least one selected from oxides and hydrated oxides of elements selected from the group consisting of aluminum, silicon, titanium, zirconium, tin and antimony coated on the surfaces of the particles.

7. Electroconductive dendrite or asteroidal titanium dioxide micro-particles comprising the dendrite or asteroidal titanium dioxide micro-particles according to claim 1 having an electroconductive layer of tin oxide containing antimony or indium oxide containing tin coated on the surfaces of the particles.

8. Electroconductive dendrite or asteroidal titanium dioxide micro-particles comprising the dendrite or asteroidal titanium dioxide micro-particles according to claim 2 having an electroconductive layer of tin oxide containing antimony or indium containing tin coated on the surfaces of the particles.

9. Electroconductive dendrite or asteroidal titanium dioxide micro-particles comprising the dendrite or asteroidal titanium dioxide micro-particles according to claim 3 having an electroconductive layer of tin oxide containing antimony or indium containing tin coated on the surfaces of the particles.

* * * * *